United States Patent [19]
Wise

[11] Patent Number: 5,597,958
[45] Date of Patent: Jan. 28, 1997

[54] METHOD FOR TESTING VISCO-ELASTIC SAMPLE BY ROTOR OSCILLATION WITHIN A DIE-FORMED CAVITY

[75] Inventor: Raleigh W. Wise, Ft. Myers, Fla.

[73] Assignee: Wise-Sullivan, Inc., Akron, Ohio

[21] Appl. No.: 585,421

[22] Filed: Jan. 11, 1996

Related U.S. Application Data

[62] Division of Ser. No. 306,174, Sep. 14, 1994, Pat. No. 5,526,693.

[51] Int. Cl.⁶ .................................................. G01N 3/24
[52] U.S. Cl. ................................................................. 73/843
[58] Field of Search ............................ 73/843, 866, 54.39

[56] References Cited

U.S. PATENT DOCUMENTS

| | | | |
|---|---|---|---|
| 3,387,490 | 6/1968 | Wise | 73/54.39 X |
| 3,488,992 | 1/1970 | Veith et al. | 374/48 |
| 4,337,646 | 7/1982 | Fraleigh | 73/54.24 |
| 4,421,424 | 12/1983 | Price et al. | 374/48 |
| 4,539,838 | 9/1985 | Fraleigh | 73/54.24 X |
| 4,829,830 | 5/1989 | Tosaki | 73/847 |
| 4,953,406 | 9/1990 | Putman | 73/843 |
| 5,163,317 | 11/1992 | Ono et al. | 73/54.39 X |

*Primary Examiner*—Thomas P. Noland
*Attorney, Agent, or Firm*—Olaf Nielsen

[57] ABSTRACT

There is disclosed a device for testing the cure properties of a visco-elastic material sample enclosed under pressure between heated dies and on the top only of a rotor. The rotor overlying a cured elastomer sealing and heat-sink member subjects the sample to oscillatory shear, and the torque is measured as an indication of the viscosity of the sample.

10 Claims, 4 Drawing Sheets

METHOD FOR TESTING VISCO-ELASTIC SAMPLE BY ROTOR OSCILLATION WITHIN A DIE-FORMED CAVITY

This is a divisional of application Ser. No. 08/306,174 filed on Sep. 14, 1994 and now U.S. Pat. No. 5,526,693.

BACKGROUND OF THE INVENTION

One classification that may be made of curemeters would include devices wherein one of two heated dies is rotated or oscillated with respect to the other, and the resulting torque of the sample measured. Among prior art patents in this group would be

| | |
|---|---|
| Veith et al | U.S. 3,488,992 (1970) |
| Uremo et al | U.S. 3,479,858 (1969) |
| Barker et al | U.S. 4,552,025 (1985) |
| Burnin et al | U.S. 5,079,956 (1992) |
| Putnam | U.S. 4,953,406 (1990) |
| Danko et al | U.S. 4,343,190 (1982) |
| Tosaki | U.S. 4,584,882 (1986) |

A second type of curemeters, and one to which the present invention primarily addresses itself, would include devices which utilize two dies, and additionally a third, rotor, member which is oscillated to derive the required test results. This group would include

| | |
|---|---|
| Prewitt et al | U.S. 4,546,438 (1985) |
| Harris et al | U.S. 3,531,996 (1970) |
| Decker | U.S. 3,681,980 (1972) |
| Price et al | U.S. 4,421,424 (1983) |
| Turner et al | U.S. 4,275,600 (1981) |
| Wise | U.S. 3,387,490 (1968) |
| Beatty et al | U.S. 3,182,494 (1965) |
| Kitchen | U.S. 4,559,812 (1985) |

Several common threads run through the disclosures of the above-mentioned test devices: the test sample materials are located on top of as well as under the rotor head, i.e. the rotor head is embedded within the rubber samples during testing; and no means are provided for sealing off the sample material from the lower die. (Additionally, in the U.S. Pat. No. 5,221,500 to Gent (1993), there is no test cavity enclosed by a pair of dies, but rather the rotor impinges directly upon the wall of the article being cured).

When a test device of the above type is opened, a substantial labor- and time-consuming effort is required to remove the sample therefrom. In practice, it is found necessary to employ metal bars and other tools to break the cured rubber from around the embedded rotor head, and this effort frequently results in tearing of the sample. This then necessitates the disassembly of the rotor from the curemeter to complete the removal of the sample, and the cleaning of any detritus which may have collected around the rotor shaft and die. When the rotor is again inserted, it is extremely difficult to seat it at exactly its former level. Thus, while the previous series of test samples may have yielded a family of test curves fairly closely related, when the testing continues with the rotor replaced, at even a slightly different height, a new curve-series will be generated, slightly differently located. This will be further referred to hereinbelow.

The above procedures unnecessarily prolong the time the device must remain open before it is recharged with a new sample, and the result is a loss of heat which must be recovered when the device again closes. Furthermore, without the heat sink means of the present invention to provide some temperature control, unacceptable heat losses are also experienced from the rotor through its associated drive- and support-means.

The results of these shortcomings are that the successive testing of samples shows poor reproduceability of results, with test curves, as seen hereafter, which are not closely bunched together.

SUMMARY OF THE INVENTION

This invention overcomes the above disadvantages by providing a curemeter having heatable die-members closeable to create a test cavity under pressure for a rubber sample, and an oscillatable rotor between the dies. The undersurface of the rotor head and its shaft are contiguous with, and match the contour of, the surfaces of a cured, elastomeric member, or biscuit, which functions as a heat sink and, at the same time, seals out any intrusion by the sample beneath the rotor head hen the cavity is closed and pressurized. The only portion of the rotor head engaging the sample is thus its top surface.

There is disclosed a means and method for testing an elastomeric material by providing for locating a test sample only on top of the rotor head, like a cap thereon, rather than surrounding it top and bottom. This results in thinner-section samples more easily removable from the test device than the prior art samples which embed the rotor head completely.

The object of the invention is therefore to provide a test device from which test samples of thinner section are expeditiously removed from atop the rotor, which needs to remain open for an absolutely minimum time for recharging, and which is provided with sealing and heat-maintenance means; all to increase reproduceability of test results.

DETAILED DESCRIPTION OF A PREFERRED EMBODIMENT

Figure 1:
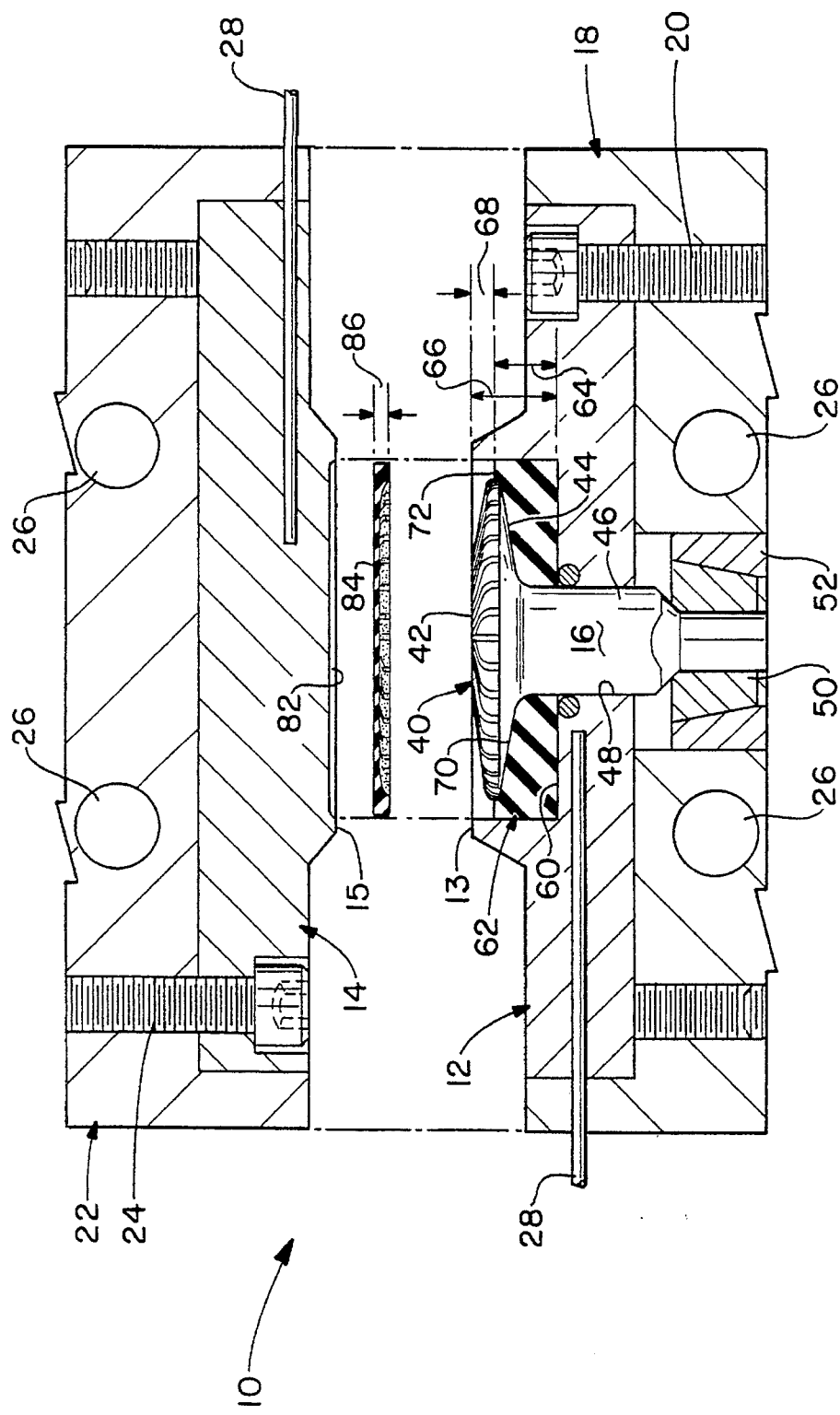
FIG. 1 is an elevational view, in cross-section, of the assembly forming a substantial portion of the curemeter of the invention, in the open position.
Figure 2:
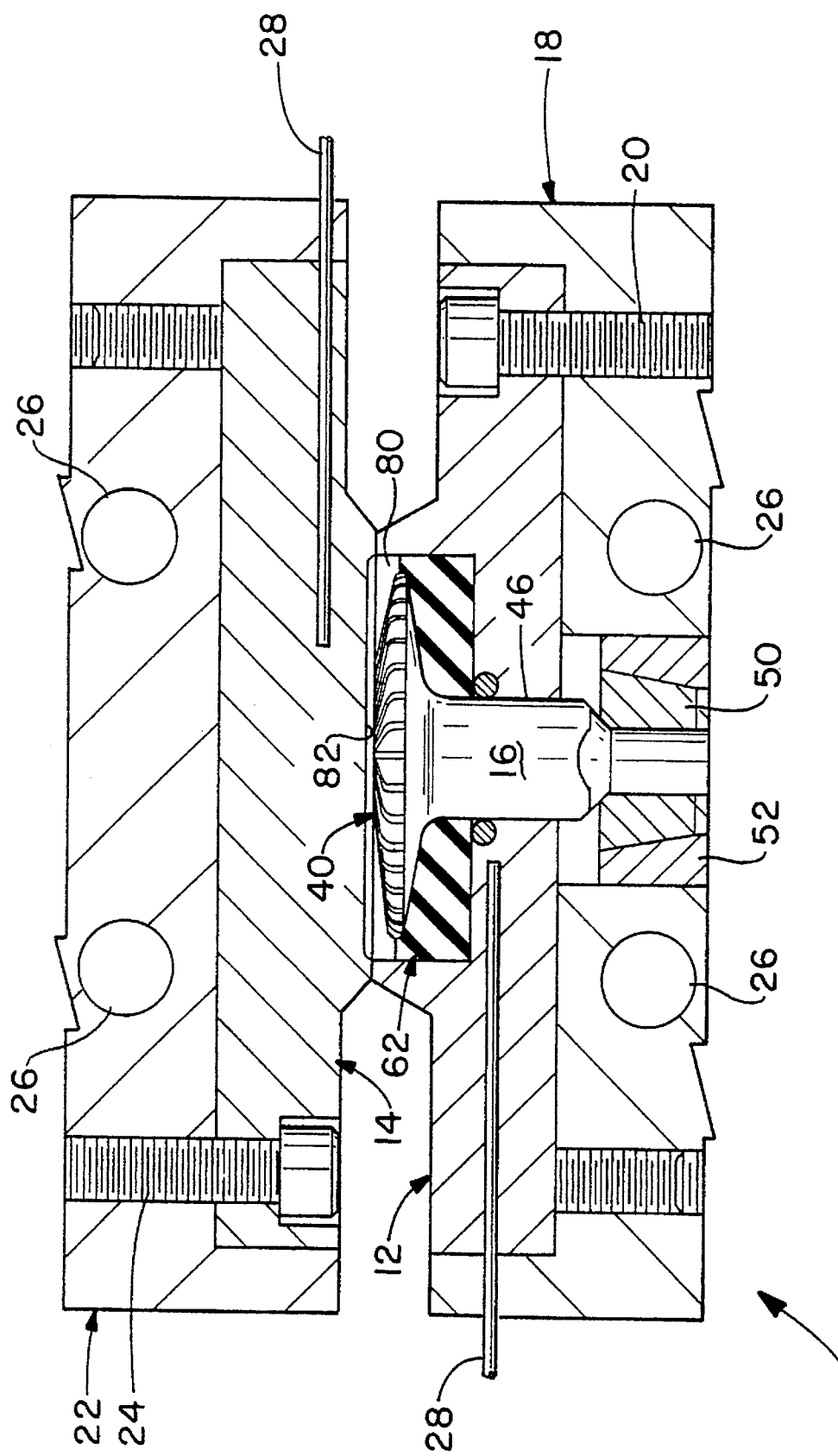
FIG. 2 is an elevational view, in cross-section, similar to FIG. 1, but with the curemeter closed.

In FIGS. 1 and 2 are shown an assembly suited for use in a curemeter such as described and shown in U.S. Pat. No. 3,531,996 (1970) to Harris et al, in the block diagram of FIG. 3; and in U.S. Pat. No. 4,546,438 (1985), to Prewitt et al, in FIG. 1. Both patents are of the second type mentioned hereinbefore.

Referring specifically to FIGS. 1 and 2, there is shown at 10 an assembly having a circular lower metal die 12 and a circular upper metal die 14, the dies having die-lands 13 and 15, respectively. Between the dies is supported a metal rotor 16. Lower die 12 is connected to lower platen 18 by threaded means 20. Similarly, upper die 14 is connected to upper platen 22 by threaded means 24.

The dies 12 and 14 are heated by heaters 26, well-known in the art and not further detailed here, and their temperatures controlled by well-known sensors 28.

The rotor 16, of heat-conductive metal, comprises a head 40 having a substantially domed or cone-shaped top face 42, here shown serrated, and an underside 44 extending at a substantial angle to the longitudinal axis of the rotor 16. A shaft 46 extending from the underside 44 and through opening 48 in the lower die 12 is secured, as by a threaded collet 50, to a torque shaft 52 oscillatable by drive- and eccentric-means such as shown, for example, in FIG. 1 of U.S. Pat. No. 3,531,996 and in FIG. 1 of U.S. Pat. No. 4,546,438.

Lower die 12 is provided with a deep cylindrical recess 60, which is fitted with an annular heat-sink and sealing member 62, preferably made of cured, low modulus silicone rubber; it has a main axial height 64 which is less than the depth 66 of the recess, leaving a small cylindrical portion 68 at the top of the recess, as explained hereafter. The top surface 70 of the member 62 is substantially contiguous with, and matches the contour of, the underside 44 of the rotor head 40 which it engages.

The peak of the rotor top surface 42 is leveled with the lower die-land 13. The top surface 70 extends laterally beyond the head 40 of the rotor, forming a small annular sample-support surface portion 72 of the member 62 which separates the rotor head from the cylindrical wall portion 68, and also prevents metal-to-metal contact between the recess wall and the rotor head.

When the dies 12 and 14 are moved into closed position, a test cavity 80 (see FIG. 2) is created substantially between the portion 68 of the lower die 12, the seal portion 72, the rotor top surface 42, and the recess 82 in the upper die 14. The sample formed therein is seen at 84 in FIG. 1, and has an edge thickness 86 substantially less than the main height 64 of the seal member 62. In a useful relationship, the seal height 64 is approximately three times the edge thickness 86. This ensures that, as the oscillation proceeds, the rotor head will tend to flex the heat-sink/seal material, rather than slipping over its surface. Although the seal contributes some torque to the sample measurement, a correction for this can be readily, if desired, be calculated, using the technique described by Gent and Xie [Rubber Chemistry & Technology, 66, 83 (1993)].

The volume of sample material charged into the device is usually slightly greater than the capacity of the cavity 80, and the closing together of the dies under pressure will therefore normally result in a small amount of the sample being squeezed out or extruded between the die-lands 13 and 15.

The top surface of portion 72 of the heat sink/sealing member 62 is lower than the level of the die-land 13 by the amount of portion 68 to ensure that seal material will not be squeezed out between the die-lands together with any excess sample material.

Figure 3:
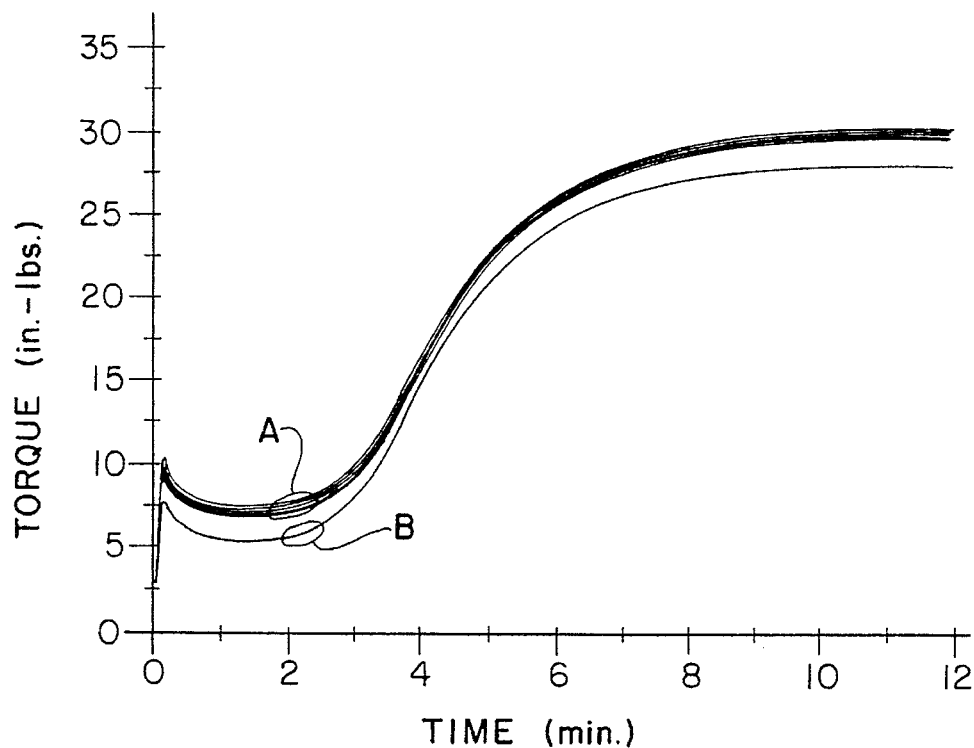
FIG. 3 is a graphical representation of curemeter curves, plotting time in minutes versus torque in inch-pounds, obtained from a prior art device.

In FIG. 3 is shown graphically a number of tests conducted according to ASTM Standard Test Method D-2084-91, wherein the biconical head of a disk rotor is completely embedded in a rubber sample. The curves generated are the typical S-curves obtained with ASTM 2084-91; since the sample totally surrounds the biconical rotor-head, its volume and gauge are shown to cause the torque to range upwards toward 35 inch-pounds. Time is plotted toward 12 minutes. It will be noted that one family of curves is designated "A". It represents a number of test-cycles, the last one of which necessitated removal of the rotor from the curemeter in order to remove all of the cured sample. The rotor and the area of the lower die where the rotor shaft is inserted was cleaned off, and the rotor re-inserted in the curemeter, but now it was not possible to fix its axial location exactly as before. Consequently, the next sample, shown by curve "B" and representing a family of test results which will obtain until the rotor must next be removed for servicing, is seen to show an entirely new range of values. Reproduceability of test results is thus poor. Even the curves of family "A" show, for example minimum torque values ranging over almost one-half inch-pound.

Figure 4:
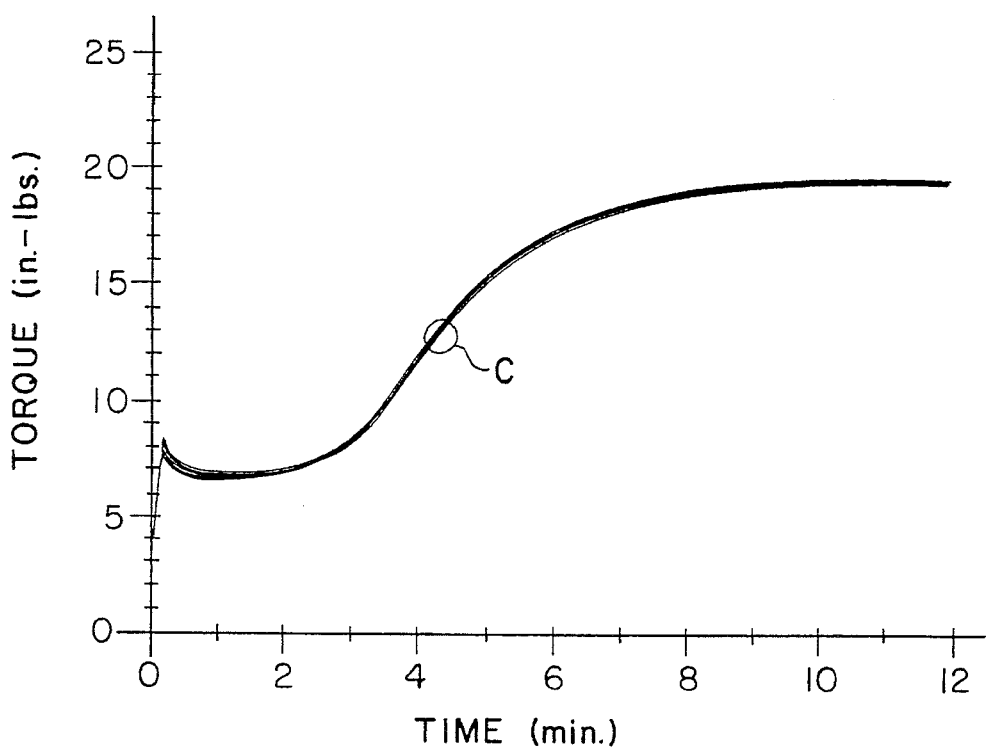
FIG. 4 is a graphical representation of curemeter curves similar to those of FIG. 3, but obtained from a device according to the invention.

In FIG. 4, the same rubber compound as in FIG. 3 is subjected to testing in the device of the invention, the sample here being thinner than in the previous tests, since it is loaded into the curemeter only on the top of the rotor, and is sealed from intrusion under the head of the rotor by the contiguous seal/heat-sink. Thus, the torque values extend only toward 25 inch-pounds. It will be noted that the family of curves "C" tracks closely, and there are no rogue aberrations as in FIG. 3. Good reproduceability of test results has now been obtained. Minimum torque values vary less than approximately one third inch-pound.

Figure 5:
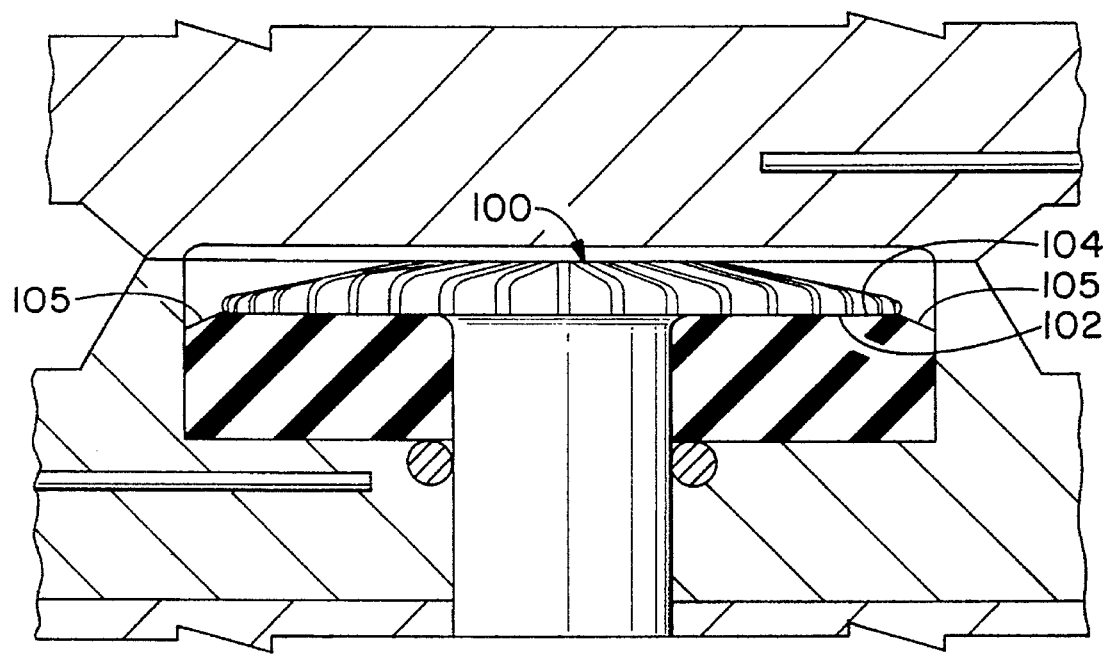
FIG. 5 is a partial, cross-sectional view showing a modification of the inventive device.

FIG. 5 shows a modification wherein the rotor head 100 has a planar underside 102 contiguous with, and matching the contour of, the top planar surface 104 of the seal 106. The laterally extending annular band portion 105 is shown canted slightly toward the bottom of the recess.

Although the dies 12 and 14 are shown as circular, the recess 60 and its wall section 68 as cylindrical, and the heat sink/seal 62 and band 72 as annular, it will be understood that other shapes may be used successfully, and that other modifications may occur to those skilled in the art without departing from the scope of the invention.

What I claim is:

1. In the method for testing a visco-elastic sample by oscillating a rotor against it within a sample cavity formed between the rotor and one of a pair of dies, and measuring the torque in the rotor as an indication of the state of cure of the sample, the improvement comprising providing a deep recess in the other one of the pair of dies, providing in the recess a cured, elastomeric seal member having a thickness substantially greater than edge height of the sample cavity, engaging an underside of a head of the rotor against the seal member, and charming sample material onto the head of the rotor, but exclusively on a top surface thereof.

2. The method of claim 1, and providing a seal member having a thickness approximately three times that of the sample.

3. The method of claim 1, and providing an annular sample-material support surface laterally beyond the head of the rotor.

4. The method of claim 1, wherein the the entire underside of the rotor head engages the seal member.

5. The method of claim 1, wherein the seal member provided has a thickness substantially less than the depth of said recess.

6. The method of claim 1, wherein the the engagement between the rotor head and the seal member is planar.

7. The method of claim 1, wherein the engagement between the rotor and the seal member extends at a substantial angle to the rotor axis.

8. In a method for testing a visco-elastic sample by rotating a rotor head against it within a cavity formed between a pair of dies, the improvement comprising providing a deep recess in one of the dies, providing in the recess an elastomeric seal member, providing engagement of the seal member with one side of the rotor head, and charging sample material onto the other side of the rotor head.

9. The method of claim 8, wherein the engagement of the seal member is provided with the underside of the rotor head, and the sample material is charged onto the top face of the rotor head.

10. The method of claim 8, wherein the sample material is charged onto the top face only of the rotor head.

\* \* \* \* \*